United States Patent
Stockham

(10) Patent No.: US 9,096,629 B2
(45) Date of Patent: Aug. 4, 2015

(54) PROCESS OF FORMING IRON HYDROXYPYRONE COMPOUNDS

(75) Inventor: Michael Arthur Stockham, Saffron Walden (GB)

(73) Assignee: Iron Therapeutics Holdings AG, Wollerau (CH)

( * ) Notice: Subject to any disclaimer, the term of this patent is extended or adjusted under 35 U.S.C. 154(b) by 0 days.

(21) Appl. No.: 13/981,551

(22) PCT Filed: Jan. 26, 2012

(86) PCT No.: PCT/GB2012/050160
§ 371 (c)(1),
(2), (4) Date: Dec. 13, 2013

(87) PCT Pub. No.: WO2012/101442
PCT Pub. Date: Aug. 2, 2012

(65) Prior Publication Data
US 2014/0088064 A1    Mar. 27, 2014

(30) Foreign Application Priority Data
Jan. 27, 2011    (GB) .................................. 1101370.3

(51) Int. Cl.
| | | |
|---|---|---|
| *C07F 15/02* | (2006.01) | |
| *A61K 31/351* | (2006.01) | |
| *A61K 33/26* | (2006.01) | |
| *C07D 309/40* | (2006.01) | |

(52) U.S. Cl.
CPC ............. *C07F 15/025* (2013.01); *A61K 31/351* (2013.01); *A61K 33/26* (2013.01); *C07D 309/40* (2013.01)

(58) Field of Classification Search
CPC ... A61K 31/351; A61K 33/26; C07D 309/40; C07F 15/025
USPC .......................................... 549/206; 514/184
See application file for complete search history.

(56) References Cited

U.S. PATENT DOCUMENTS

| | | | |
|---|---|---|---|
| RE37,534 E | 1/2002 | Hider et al. | |
| 6,339,080 B1 | 1/2002 | Stockham et al. | |
| 6,635,631 B2 | 10/2003 | Stockham et al. | |
| 7,459,569 B2 * | 12/2008 | Stockham ..................... | 549/210 |

FOREIGN PATENT DOCUMENTS

| | | | |
|---|---|---|---|
| CN | 1408364 A | 4/2003 | |
| EP | 0 107 458 A1 | 5/1984 | |
| EP | 0120670 A1 | 10/1984 | |
| EP | 0 159 194 A3 | 10/1985 | |
| GB | 2 128 998 A | 5/1984 | |
| GB | 2 136 806 A | 9/1984 | |
| GB | 2136806 A | 9/1984 | |
| GB | 2 157 563 A | 10/1985 | |
| WO | 03/097627 A1 | 11/2003 | |
| WO | 2009/138761 A1 | 11/2009 | |

OTHER PUBLICATIONS

Ahmet et al., "A Potential Iron Pharmaceutical Composition for the Treatment of Iron-deficiency Anemia. The Crystal and Molecular Structure of mer-tris(3-hydroxy-2-methyl-4H-pyran-4-onato)iron(III)," J. Chem. Soc., Dalton Trans., 1988, 1159-1163.

Mukha et al., "Synthesis and Properties of Metal Chelates Based on Natural gamma-Pyrone Maltol," Chemistry for Sustainable Development 15 (2007) 448-458.

Nurchi et al., "Iron(III) and aluminum(III) complexes with hydroxypyrone ligands aimed to design kojic acid derivatives with new perspectives," J Inorg Biochem., 2010, 104(5):560-9.

International Search Report and Written Opinion for PCT International Application No. PCT/GB2012/050160, mailed Apr. 24, 2012.

Abdel-Razeq et al., "Parental Ferric Hydroxide Saccharate Therapy for Iron Deficiency Anemia: Safety and Efficacy," Blood (ASH Ann. Meeting Abstracts) 104:Abstract 3681 (2004).

Ahmet et al., "A Potential Iron Pharmaceutical Composition for the Treatment of Iron-Deficiency Anaemia. The Crystal and Molecular Structure of mer-Tris-(3-hydroxy-2-methyl-4H-pyran-4-onato) Iron (iii)," J. Chem. Soc. 5:1159-1163 (1988).

Antipova et al., "Al(III)-Maltol Complexes, Structure and Stability," Chem. Sustain. Dev. 13:377-381 (2005).

Batterman et al., "Use of Colloidal Iron Hydroxide for the treatment of Hypochromic Anemia. Notes on Incidence of Gastro-Intestinal Irritation with Iron Therapy," Am. J. Med. Sci. 214(3):268-271 (1944).

Kidani et al., "Synthesis of Maltol-Fe(III) Complex," Nagoya-shiritsu Daigaku Yakugakubu Kenkyu Nenpo, (1964-1992) (1970) (18) pp. 16-21 (abstract only).

Gerard et al., "Iron(III) Complexes of Maltol (3-Hydroxy-2-methyl-4-pyrone), Including Hydroxo-Complexes, in an Acidic Medium," J. Chem. Res. 9:314 (1980) (synopsis).

Mukha et al., "Synthesis and Properties of Metal Chelates Based on Natural (Gamma)-Pyrone Maltol," Chem. Sustan. Dev. 15:448-458 (2007).

(Continued)

*Primary Examiner* — Andrew Kosar
*Assistant Examiner* — John Mauro
(74) *Attorney, Agent, or Firm* — LeClairRyan, a Professional Corporation

(57) ABSTRACT

The invention provides a method of forming an iron hydroxypyrone compound comprising reacting a hydroxypyrone with a non-carboxylate iron salt in an aqueous solution, and precipitating the iron hydroxypyrone compound from the aqueous solution having a pH of greater than 7.

9 Claims, No Drawings

(56) References Cited

OTHER PUBLICATIONS

Nurchi et al., "Iron(III) and Aluminum(III) Complexes with Hydroxypyrone Ligands Aimed to Design Kojic Acid Derivatives with New Perspectives," J. Inorg. Biochem. 104:560-569 (2010).
Spielman et al., "A Synthesis of Maltol," J. Am. Chem. Soc. 69:2908 (1947).
Search Report for Great Britain Patent Application No. 1101370.3 (Apr. 28, 2011).
International Search Report for Application Serial No. PCT/GB2012/050160 (Apr. 13, 2012).
International Preliminary Report for Application Serial No. PCT/GB2012/050160 (Aug. 8, 2013).
Search Report for Great Britain Patent Application No. 1101370.3 (Jun. 6, 2011).
Examination Report for Australia Application No. 2012210337 (Jan. 23, 2014).
Written Opinion for Singapore Application No. 201305698-1 (Aug. 27, 2014).
Office Action for China Application No. 201280006090.4 (Jun. 27, 2014).
Written Opinion for Singapore Application No. 201305698-1 (Mar. 13, 2015).

* cited by examiner

PROCESS OF FORMING IRON HYDROXYPYRONE COMPOUNDS

This application is a national stage application under 35 U.S.C. §371 of PCT Application No. PCT/GB2012/050160, filed Jan. 26, 2012, which claims the priority benefit of Great Britain Patent Application No. GB1101370.3, filed Jan. 27, 2011.

The present invention relates to a method of forming iron hydroxypyrone compounds and to compounds and compositions obtainable by the method.

U.S. Pat. No. 6,339,080 and U.S. Pat. No. 6,635,631 describe the formation of iron complexes of 3-hydroxy-4-pyrones where a carboxylic acid is provided as a counterion.

EP 0159194 discloses neutral (i.e., charge balanced) ferric iron complexes comprising specified combinations of ligands selected from 3-hydroxypyrones, 3-hydroxypyridones and specific mono-carboxylic acids. In order to produce neutral (i.e., charge balanced) ferric complexes, EP 0159194 discloses the reaction of an ethanolic solution of ferric chloride with a chloroform solution of a hydroxypyrone ligand followed by adjustment of the pH with solid sodium carbonate.

GB 2128998, GB 2157563, and EP 0107458 all describe a method of preparation of neutral (i.e., charge balanced) iron (III) maltol complexes which involves mixing a solution of maltol in chloroform with a 1M solution of ferric chloride in ethanol to provide a 3:1 molar ratio of maltol:iron in the mixture. After 5 minutes at 20° C. a 10 molar excess of solid sodium carbonate is added to the solution and the mixture is stirred for 10 minutes. The mixture is then filtered and solvent evaporated to give the neutral complex containing maltol and the ferric cation in 3:1 proportion. Recrystallisation of the 3:1 complex from ethanol provides the pure neutral ferric complex.

GB 2136806 describes the preparation of an iron hydroxypyridone complex using freeze drying and organic solvents.

WO 03/097627 discloses a method of forming an iron hydroxypyrone compound comprising reacting an iron salt of a carboxylic acid and a hydroxypyrone in an aqueous solution at a pH greater than 7.

Nurchi et al (Journal of Inorganic Biochemistry, 104, 2010, 560-569) describes the synthesis of a ferric tri-kojic acid chelate which is very soluble in the solution and so does not precipitate.

Batterman at al (American Journal of the Medical Sciences, 1947, 214(3), 268-271) discloses the use of colloidal iron hydroxide for the treatment of hypochromic anemia.

Hikmat et al (Blood (ASH Annual Meeting Abstracts) 2004 104: Abstract 3681 describes the use of parental ferric hydroxide saccharate therapy for iron deficiency anemia.

Gerard et al (J. Chem. Research (S), 1980, page 314) discloses iron (III) complexes of maltol (3-hydroxy-2-methyl-4-pyrone) including hydroxo-complexes, in an acidic medium.

Ferric Chloride has been used (see Y Kidani, R Salto and Hisashi Koike 1970 Annual report of College of Pharmacy 1970) as a starting material for the synthesis of Ferric Trimaltol.

Ferric chloride is an attractive starting material because it is cheap, stable and readily available. However, attempts to improve the synthesis of ferric trimaltol have been hindered by the fact that ferric chloride is most soluble at acid pH values while maltol is most soluble at alkaline pH values.

S A Mukha et al (Chemistry of Sustainable Development 15, (2007) 448-458) describes the use of organic solvents to overcome a basic problem of incompatibility of ferric chloride and maltol in an aqueous medium.

This process using organic solvents would be looked on unfavourably by regulatory authorities if used commercially. It would also be an extremely expensive process using evaporation procedures and the measures that would be required to obtain a reproducible batch product that could be manufactured to GMP (Good Manufacturing Process) standards.

The above processes for producing neutral ferric complexes of hydroxypyrone have several drawbacks. The first of these is that the process requires the use of organic solvents. Organic solvents are expensive, toxic and flammable. Furthermore, the organic residues obtained as a result of the process have to be disposed of, which requires further expense and safety measures.

There remains a need for further methods of forming iron hydroxypyrone compounds, such as iron hydroxypyrone compounds having pharmaceutical purity, which methods avoid or reduce some or all of the above-mentioned problems associated with the known methods for producing neutral (i.e., charge balanced) ferric hydroxypyrone complexes. In particular, there is a need to avoid the use of organic solvents in the process, and/or to avoid previous impurities and/or to increase the yield of the ferric hydroxypyrone and/or to reduce the overall amount of solvent required for the reaction.

In a first aspect of the invention, there is provided a method of forming an iron hydroxypyrone compound comprising reacting a hydroxypyrone with a non-carboxylate iron salt in an aqueous solution, and precipitating the iron hydroxypyrone compound from the aqueous solution and/or, preferably optionally, the aqueous solution has a pH of greater than 7, preferably a final pH greater than 7.

In a second aspect of the invention, there is provided a method of forming an iron hydroxypyrone compound comprising reacting a hydroxypyrone with a non-carboxylate iron salt in an aqueous solution at a pH greater than 7 and precipitating the iron hydroxypyrone from the aqueous solution, wherein, optionally, the method does not comprise the use of an organic solvent and/or the solution does not comprise a buffer.

In a third aspect of the invention, there is provided a method of forming an iron hydroxypyrone compound comprising reacting a hydroxypyrone in an aqueous alkaline solution with a non-carboxylate iron salt, or a mixture of a hydroxypyrone and a non-carboxylate iron salt, wherein the salt or mixture is added to the aqueous alkaline solution and, optionally, precipitating the iron hydroxypyrone from the aqueous alkaline solution.

In a fourth aspect of the invention, there is provided a method of forming an iron hydroxypyrone compound comprising reacting an aqueous solution of a hydroxypyrone having a temperature of greater than 40° C. to 100° C., with a non-carboxylate iron salt and, optionally, adding further hydroxypyrone and/or, optionally, precipitating the iron hydroxypyrone from the aqueous solution.

In a fifth aspect of the invention, there is provided a method of forming an iron hydroxypyrone compound comprising reacting an aqueous solution of a hydroxypyrone having a temperature of greater than 40° C. to 100° C. with a non-carboxylate iron salt, optionally cooling, and reacting the solution with an aqueous alkaline solution comprising a hydroxypyrone and, optionally, precipitating the iron hydroxypyrone from the aqueous alkaline solution.

In another aspect of the invention, there is provided a method of forming an iron hydroxypyrone compound comprising reacting a hydroxypyrone with a non-carboxylate iron salt in an aqueous solution and precipitating the iron hydroxypyrone compound from the aqueous solution having a pH of greater than 7 or lower than or equal to 7 such as defined herein. Optionally, when the pH is lower than or equal to 7, as defined herein, the solution does not comprise a buffer as defined herein and/or the molar ratio of hydroxypyrone to iron salt used is greater than 3:1, such as 3.1:1, 3.5:1, 4:1 or higher.

In a sixth aspect of the invention, there is provided a pharmaceutical composition comprising an iron hydroxypyrone compound and an iron hydroxide. The pharmaceutical composition is generally suitable for administration to a subject, such as a mammal, for example a human. The route of administration is typically oral.

The present invention provides methods in which the iron hydroxypyrone, such as ferric trimaltol, can be precipitated from an aqueous solution or an aqueous alkaline solution. Furthermore, the non-carboxylate iron compound as a starting material can yield a sodium or potassium salt of high solubility to enable easy removal from the final product in the aqueous environment. The sodium or potassium salt may also be non-toxic, e.g chloride.

The method of the invention can avoid the formation of black deposits and gums consisting of ferric chloride/ferric hydroxide polymers, as well as non-red precipitates, and mixed iron hydroxy and chloride species, such as, for example, $Fe(OH)_2(Maltol)$ and $Fe(OH)(Maltol)_2$.

In one embodiment, the invention provides a method of forming an iron hydroxypyrone compound wherein iron hydroxide, such as ferric hydroxide, is present in an amount of less than or equal to about 10 wt. % based on the weight of the iron hydroxypyrone compound, such as less than or equal to about 5 wt. % or about 2 wt. %.

In one embodiment of the invention, the iron hydroxypyrone compound is a pharmaceutically pure compound. For example, the iron hydroxypyrone compound may have a purity of greater than or equal to about 95, 96, 97, 98, 99 or 99.5%. It is preferred that the iron hydroxypyrone compound which is precipitated or precipitated and isolated and, optionally, dried, has a purity of greater than or equal to about 95, 96, 97, 98, 99 or 99.5%, preferably without further purification.

The term "precipitating" as used herein includes an active step of causing the iron hydroxypyrone to be precipitated by, for example, increasing the pH of the aqueous solution to greater than 7 and/or adding hydroxypyrone. However, it will be understood by a person skilled in the art that the iron hydroxypyrone compound can precipitate spontaneously if the reaction conditions are suitable and without the need to carry out additional steps. For example, the solubility of the iron hydroxypyrone may be less than that of the reactants in the aqueous solution causing it to precipitate when the reactants are combined. Therefore, the term "precipitating" also includes the passive embodiment of allowing the iron hydroxypyrone to precipitate.

In one embodiment of the invention, the step of precipitating comprises increasing the pH of the aqueous solution from a pH of less than 7, such as from 3 to 6 or 4 to 5, to greater than 7, such as defined herein, and/or adding additional hydroxypyrone to the aqueous solution comprising an iron salt and hydroxypyrone. The amount of additional hydroxypyrone may be, for example, sufficient to form a molar ratio of iron salt to hydroxypyrone of about 1:3 or greater. So, the amount of additional hydroxypyrone may be at least the molar amount of the iron salt, such as at least one or two times the molar amount of the iron salt.

Alternatively, the step of precipitating comprises combining the iron salt and hydroxypyrone in a molar ratio of about 1:3 or greater in an aqueous solution at a pH of greater than 7, such as defined herein. The aqueous solution generally comprises at least 60% v/v water as solvent in such an embodiment, for example from 70 to 100% v/v, such as about 100% v/v.

In one embodiment, the step of precipitating comprises combining the iron salt and hydroxypyrone in an aqueous solution at a pH of greater than 7, wherein the aqueous solution comprises at least 60% v/v water as solvent, for example from 70 to 100% v/v, such as about 100% v/v.

In another embodiment, the step of precipitating the iron hydroxypyrone comprises the combination of the iron salt and hydroxypyrone.

The term "precipitate" includes a solid phase of the iron hydroxypyrone, which can be distinguished and separated from the liquid aqueous phase or solution. The solid phase can be amorphous or crystalline or mixtures thereof. In general the iron hydroxypyrone is formed as a burgundy red solid.

In one embodiment of the invention, the precipitated iron hydroxypyrone compound is separated and collected from the solution, which, optionally does not comprise any organic solvent as defined herein. The separation and collection may be carried out using any suitable means known in the art such as, for example, filtration, for example, filtration under ambient or reduced pressure (for example, less than 1 bar) or under vacuum, or by centrifugation or decanting. By the term "vacuum", as used herein, it is meant to include pressures of from, for example 100 nPa to 100 kPa, such as from 100 mPa to 3 kPa or from 3 kPa to 70, 80 or 90 kPa.

The term "aqueous solution" includes solutions in which the solvent comprises water. The solution is typically primarily composed of water, such as greater than 30%, 40%, 50%, 60% v/v water, or greater than 70%, 80% or 90% v/v water, for example from 60 to 100% v/v water, or from 80 to 98% v/v water, such as from 85 to 95% v/v water based on the total volume of solvent or solution. In one embodiment of the invention, the solvent of the aqueous solution comprises or is water. The water may be distilled water.

In one embodiment, the aqueous solution in which the reaction takes place and from which the precipitation occurs is the same aqueous solution. Typically, the method of the invention does not involve removal of the solvent from the aqueous solution, such as by rotary evaporation, and replacement with another solvent, such as an organic solvent.

In one embodiment of the invention, the solvent of the aqueous solution is not removed under reduced pressure or evaporated. In another embodiment, the aqueous solution is not freeze-dried.

In one embodiment, the aqueous solution may comprise solvents other than water provided that they do not affect the ability of the iron hydroxypyrone to precipitate from the aqueous solution. For example, the aqueous solution may comprise an alcohol, such as ethanol. The amount of non-water solvent may be less than 20% v/v, such as less than 10% v/v.

In one embodiment of the invention, the concentration of hydroxypyrone, such as maltol, in the aqueous solution is greater than 0.03 M, such as from 0.04 to 2M, for example from greater than 0.08 to 1.5 or 1 M. The concentrations of the iron salt and hydroxypyrone may be such as to provide a molar ratio of iron to hydroxypyrone in the range of about 5:1 to about 1:5, such as about 3:1 to about 1:3. For example the molar ratio of iron to hydroxypyrone may be about 1:3 or higher, such as about 1:3 in the aqueous solution. The molar concentration of the iron salt may be greater or less than the molar concentration of hydroxypyrone but is generally less.

Typically, the aqueous solutions used are substantially free of organic solvents such as for example, alcohols, such as methanol and ethanol, as well as ketones such as acetone, and halogenated solvents, such chloroform and dichloromethane or esters such as ethyl acetate. By the term "substantially free" it is intended to mean that the aqueous solution comprises less than 10% (preferably less than 5%, more preferably less than 1%, most preferably, substantially 0%) of organic solvent volume by volume (v/v) of the total aqueous solution.

In one embodiment of the invention, the method does not comprise the use of an organic solvent, such as defined above. For example, no organic solvent may be used to form the iron hydroxypyrone compound as well as to isolate and/or purify the iron hydroxypyrone compound.

The aqueous solution in the methods of the invention is also generally substantially free of buffers, such as citrate, acetate, glycine and morpholine propane sulphonate (MOPS) and the like. The term substantially free is as defined above. In one embodiment, the aqueous solution does not comprise a buffer and the method is carried out in the absence of a buffer.

Advantageously, the iron hydroxypyrone, as defined herein, such as ferric trihydroxypyrone, is produced in an amount of greater than 5 g, for example, greater than 10 g, 50 g, 100 g or 1 Kg, such as from 10 g or 100 g to 10 Kg or 50 g or 500 g to 5 Kg in the methods of the invention.

In one embodiment, the method comprises reacting the hydroxypyrone with a non-carboxylate iron salt in an aqueous alkaline solution. By "aqueous alkaline solution" it is intended to mean an aqueous solution, such as defined herein, having an initial and/or final pH of greater than 7.

The term "initial pH" generally refers to the pH of the solution before the addition of the iron salt or solution thereof as well as the hydroxypyrone. The term "final pH" generally refers to the pH of the solution after the iron salt or solution thereof is added, or a mixture including the iron salt and hydroxypyrone, and the iron hydroxypyrone is formed. The aqueous alkaline solution generally comprises a base, such as defined herein.

Typically, the pH of the solution is not buffered, so the pH of the solution may vary during the process from the initial value, although in one embodiment it can be. Generally, the initial pH and the final pH are both greater than 7, such as defined herein, although the pH may decrease below 7 during at least part of the reaction. In that case, the pH may be adjusted to above 7 in order to precipitate the iron hydroxypyrone from an aqueous solution.

In one embodiment of the invention, the pH of the aqueous solution is greater than about 3, 4, 5, 6, 7, 8, 9 or 10 throughout all of the reaction. For example the pH of the aqueous solution is preferably greater than about 7 over the course of the reacting.

In one embodiment of the invention, the pH of the aqueous solution is not adjusted, such as by the addition of base, for example, sodium hydroxide or sodium carbonate, following combining the iron salt and the hydroxypyrone.

In one embodiment of the invention, the non-carboxylate iron salt and a hydroxypyrone are reacted in an aqueous solution at a pH greater than 7. This aqueous solution and all aqueous solutions discussed herein are preferably prepared using deionised water or distilled water. It is particularly preferred if the solutions are prepared using distilled water.

The aqueous solution in which the reaction between the iron salt and the hydroxypyrone takes place is preferably at an initial and/or final pH greater than about 7.2, 8, or preferably greater than about 9, more preferably at an initial and/or final pH greater than about 10. In one embodiment, the pH of the solution is at an initial and/or final pH in the range of from about 7.1 to about 14, or from 7.1 to 10, 11 or 12, more preferably from about 7.3, 7.5 or about 9.1 to about 13, particularly preferably from about 10 to about 13, such as during the method.

In one embodiment, the pH of the aqueous solution is greater than 7 to less than 11 or 10, for example about 7.2 to 9, such as 7.4 to 8. This may serve to limit the production of ferric hydroxide.

The pH of the aqueous solution from which the iron hydroxypyrone precipitates may be as defined above, for example, greater than 7 to about 9, 10 or 11, such as from about 7.2 to 9 or 7.4 to 8, or greater than 8 or 9. Optionally, the pH of the aqueous solution from which the iron hydroxypyrone precipitates may be greater than 7 to less than 10 or 11. Alternatively, the pH of the aqueous solution from which the iron hydroxypyrone precipitates may be lower than or equal to 7, for example, from 5 to 7 or from 5.5 to 6. This may be particularly suitable when the molar ratio of hydroxypyrone to iron salt used is greater than 3:1, such as 3.1:1 or higher, 3.5:1 or higher or 4:1 or higher, for example, from 3.5:1 or 4:1 up to 10:1.

As described above, the pH of the aqueous solution may decrease below about 7 during at least part of the reaction between the hydroxypyrone and iron salt. In one embodiment of the method, the initial pH of the aqueous solution is less than or equal to about 7. For example, the initial pH of the solution may be from about 3 to about 7, such as from about 4 to about 6 or about 6 to about 7. The pH may then be increased to greater than 7, such as defined above. The increase of pH may be achieved by, for example, the addition of the solution to an alkaline solution, such as a solution having a pH greater than 7, such as from 8 to 11 or greater than 9 to 10. Such a solution may comprise hydroxypyrone. Alternatively, further quantities of base can be added to the solution to increase the pH.

In one embodiment of the invention, the pH of the aqueous solution does not fall below 2, 3, 4, 5 or 6 during the reaction. For example, the pH of the aqueous solution may be in the range of 2 to 13, such as 4 to 11, for example 5 to 10 or 6 to 9 during the reaction.

Any of the pH values above may be achieved by using an aqueous solution comprising a suitable base at a certain concentration. By "suitable base" it is intended to mean any base that does not form a complex to an iron cation under the reaction conditions or interfere with the reaction between the iron salt and the hydroxypyrone in any other way. The aqueous solution may comprise a single base or a mixture of two or more bases.

The pH may be measured using any of the means known to the skilled person in the art. This may include any of the commercially available electronic pH meters or universal indicator paper.

Preferably, the base is soluble in water at room temperature (e.g., from 0 to 40° C.) to the extent that it is able to provide the desired pH.

Examples of bases suitable for use in the present invention include: hydroxides, such as bases selected from the group consisting of: alkali metal hydroxides, such as sodium and potassium hydroxide, ammonium hydroxide; and sodium or potassium hydrogen carbonate or carbonate. In one embodiment, the base does not comprise a carbonate, such as sodium carbonate, or a hydrogen carbonate.

The base may be selected from the group consisting of: alkali metal hydroxides and mixtures thereof. In one embodiment, the base is selected from sodium hydroxide or potassium hydroxide and mixtures thereof, or sodium hydroxide.

The amount of base in the aqueous solution may suitably range from 0.1% to 50% w/v of the aqueous solution. Preferably, however, the amount of base ranges from 5% to 40% w/v of the aqueous solution. In one embodiment of the invention, the amount of the base, such as an alkali metal hydroxide, in the aqueous solution is from about 10 to about 20% w/v, such as about 15% w/v.

In one embodiment of the invention, the molar ratio of hydroxypyrone to iron salt in the aqueous solution is at least 3:1. Advantageously, the relative molar ratio may be in the range of 3:1 to 5:1. However, in a particularly preferred embodiment of the present invention, the molar ratio of hydroxypyrone to iron salt is 3.1:1 to 3.5:1.

In one embodiment of the invention, the molar ratio of hydroxypyrone to iron salt used is greater than 3:1, such as about 4:1 or higher. It can be desirable to provide such an excess of the hydroxypyrone, which is unreacted with iron, in the solution and the composition obtained. Also, for example, using a molar ratio of hydroxypyrone, such as maltol, to iron salt of greater than 3:1, for example, about 4:1 or higher, can reduce the formation of iron hydroxide and/or lower the pH at which precipitation of iron hydroxypyrone, such as ferric trihydroxypyrone, for example, ferric trimaltol, can occur, to for example, lower than about 7, such as from 5 to 7 or about 5.5 to 6. Lowering the pH, as specified previously, can also avoid or reduce the formation of iron hydroxide.

The person skilled in the art will appreciate that pH and the solubility of particular iron hydroxypyrone compounds in aqueous solution will also determine the nature of the iron compounds formed. Therefore, the relative molar ratio of hydroxypyrone to iron salt may be slightly less than 3:1 at higher values of pH (i.e., greater than 10) or with complexes that are less soluble in aqueous solutions in order to produce acceptable yields of iron hydroxypyrone compounds.

In one embodiment of the invention, an aqueous solution at a pH specified above is prepared by adding an amount of base to water, preferably deionised or distilled water. The concentration of base will determine the pH value and the amount of base necessary to provide a particular pH value can be calculated accordingly.

The iron salt and/or hydroxypyrone may be added to the aqueous solution at a pH specified above in a solid form. Alternatively, the iron salt and hydroxypyrone may each be added separately, in any order, or at the same time, to an aqueous solution, which does not comprise the iron salt or hydroxypyrone, in separate aqueous solutions, such as defined herein.

The present invention recognises that the way in which the iron salt and the hydroxypyrone are combined can avoid the formation of undesirable side-products, such as those described above. Typically, the iron salt is added in a solid form to an aqueous solution comprising the hydroxypyrone. However, the iron salt may be added to the hydroxypyrone in the form of an aqueous solution of the iron salt. For the iron salt, the pH of the aqueous solution is generally less than 7. For ferric salts, for example, the pH of the aqueous solution is generally in the range of 1 to 4. For ferrous salts, for example, the pH of the aqueous solution is generally in the range of 3 to 6. This pH range can help to stabilise the iron ions against hydrolysis and other forms of decomposition. In general, freshly prepared solutions of the iron salts are preferred if solutions of the iron salt are to be used.

In one embodiment of the invention, the freshly prepared solution of the iron salt is a solution which is used within about or less than 10, 9, 8, 7, 6, 5, 4, 3, 2 or 1 hours of its preparation, such as within about 30 minutes, 20 minutes or 10 minutes.

In another embodiment of the invention, the iron salt is added to an aqueous solution comprising the hydroxypyrone over a time period of from about 5 minutes to 20 hours, such as from 10 minutes to 10 hours, for example, from 30 minutes to 5 hours or 1 hour to 2 hours. For example, an aqueous solution of the iron salt may be added drop wise to the hydroxypyrone over any of the above time periods.

The reaction of the hydroxypyrone with a non-carboxylate iron salt may be carried out under ambient temperatures, such as from 5 to 35° C. In one embodiment, the method is carried out at a temperature which is higher than ambient. For example, the aqueous solution may be at a temperature of greater than 40° C., such as greater than 50° C., or 60° C. or 70° C. or 80° C. or 90° C., for example from 40 to 100° C., such as from 50 to 90° C. or 60 to 80° C. Therefore, the method may be carried out at these temperatures.

It has been, advantageously, found that the hydroxypyrones are stable at these higher temperatures where solubility is enhanced. Therefore higher concentrations of hydroxypyrones can be used which results in a precipitated product, such as following the addition of the iron salt, optionally followed by cooling to ambient temperatures.

In one embodiment, the method comprises reacting the hydroxypyrone with a non-carboxylate iron salt at a temperature of greater than about 40° C. such as greater than about 50° C., or about 60° C. or 70° C. or 80° C. or 90° C. or as defined above. The aqueous solution may have a pH of from about 6 to about 8, such as about 7 at these temperatures or a pH of greater than 7, as defined above.

The non-carboxylate iron salt is typically added to the hydroxypyrone in the methods of the invention. The hydroxypyrone is generally in an aqueous alkaline solution as defined herein but it may be at a pH of less than or equal to 7, such as from 3 to 7, at least initially.

In one embodiment, the non-carboxylate iron salt is added to the hydroxypyrone, such as in an aqueous solution as defined herein. For example, the hydroxypyrone may be in an aqueous solution, such as an aqueous alkaline solution, to which the non-carboxylate salt is added. Alternatively, the hydroxypyrone may be combined with an aqueous solution, such as water, that is not necessarily alkaline, the solution is heated, such as to a temperature indicated above, and the non-carboxylate salt is combined with the heated solution. The resulting solution may be combined with a, separate, aqueous alkaline solution comprising the hydroxypyrone. For example, the heated solution may be added to an aqueous alkaline solution comprising the hydroxypyrone.

The iron salt and the hydroxypyrone may be combined with the aqueous solution, such as defined above, prior to heating to, for example, greater than 60° C., and then combined with a, separate, aqueous alkaline solution comprising the hydroxypyrone. The aqueous alkaline solution may have any pH as defined above.

The pH of the solution may then be adjusted to greater than 7 in order to precipitate the iron hydroxypyrone and/or additional hydroxypyrone may be added as described above.

Thus, in one embodiment, a 1:1 and/or 1:2 iron hydroxypyrone complex, that is an iron monohydroxypyrone, an iron dihydroxypyrone compound, or a mixture thereof, is formed at a pH less than or about 7 by reaction of the hydroxypyrone and the iron salt. The molar ratio of iron to hydroxypyrone may be from about 1:1 to 1:2. The pH of the solution can then be adjusted to greater than 7 in order to precipitate the iron hydroxypyrone. Alternatively, or in addition, the aqueous solution comprising a 1:1 and/or 1:2 iron hydroxypyrone complex can be reacted with an additional amount of the hydroxypyrone compound to precipitate the iron hydroxypyrone compound. The additional amount of the hydroxypyrone may be as described above, that is sufficient to form the 1:3 iron hydroxypyrone complex.

Thus, the method of the invention may comprise a first step of forming an iron mono or dihydroxypyrone complex, or mixtures thereof, by reacting the iron salt with a hydroxypyrone, such as where the ratio of the molar concentration of the iron salt to the hydroxypyrone is greater than 1:3, such as 1:1, 2:1, 3:1 or 5:1, and a second step of forming an iron trihydroxypyrone compound by the addition of further hydroxypyrone and/or adjusting the pH to greater than 7, such as defined herein. The further hydroxypyrone may be any amount sufficient to form the iron trihydroxypyrone, or 1:3 iron hydroxypyrone complex, such as described above. There is no need to isolate the "intermediate" iron mono or dihydroxypyrone complex although this could be done and the reaction completed at a later stage.

In one embodiment of the invention an iron monohydroxypyrone, an iron dihydroxypyrone, or a mixture thereof, is formed by reacting the hydroxypyrone with a non-carboxylate salt at an initial pH of less than 7 and/or additional hydroxypyrone compound is added to the aqueous solution and/or the pH is increased to greater than 7.

In one embodiment of the invention, the hydroxypyrone and non-carboxylate iron salt are reacted in an aqueous solution having a pH in the range of, for example, 3 to 7, such as 4 to 5. The pH of the solution is then increased to greater than 7, for example, 7.2 to 9 or 7.4 to 8, in order to precipitate the iron hydroxypyrone compound, such as ferric trihydroxypyrone, from the solution. The molar ratio of the hydroxypyrone to non-carboxylate iron salt used is preferably in the range of greater than or equal to 3:1, for example, 5:1 to 3.1:1, such as about 4:1 or higher. All of the hydroxypyrone may be used initially at the low pH or a portion may be combined later, such as before, the same time or after the pH is increased.

At a pH of 3 to 7 the hydroxypyrone and non-carboxylate iron salt may react to form predominantly "protonated" complexes i.e., positively charged hydroxypyrone complexes with iron in which the molar ratio of iron to hydroxypyrone is 1:1 or 1:2. These can have a relatively higher solubility in aqueous solution compared to the neutral 1:3 complexes. Increasing the pH can increase the amount of neutral complex with a lower solubility and this can precipitate.

The term "non-carboxylate iron salt" is intended to refer to iron salts, such as ferrous and ferric salts, which do not comprise carboxylate anions such as those described in WO 03/097627. The non-carboxylate iron salts therefore generally comprise iron salts of inorganic anions, such as chloride, nitrate and sulphate. An aqueous solution of the non-carboxylate iron salt typically has a pH of less than 7, such as from 0 to 6, 1 to 5, 2 to 4 or about 3. The iron salt typically has a solubility in water of at least 20 g/100 ml water at 20° C., such as at least 40 g/100 ml water.

In one embodiment, the non-carboxylate iron salt is in the form of a solid, such as a powder, or an aqueous solution of the salt, where the aqueous solution is as defined herein. The aqueous solution of the iron salt generally has a pH of less than 7, such as from 0 to 7, 1 to 6, 2 to 5 or 3 to 4. The solid or solution may be combined with or added to the hydroxypyrone, such as in an aqueous solution or an aqueous alkaline solution, in one or more steps or stages. For example, a portion of the iron salt may be added, followed by the addition of base to adjust the pH and optionally a further portion of the iron salt.

The non-carboxylate iron salt and the iron hydroxypyrone compound may be independently pharmaceutically acceptable or non-toxic.

The iron salts of the invention generally include inorganic anions, that is the anions do not comprise carbon and hydrogen. In one embodiment, the non-carboxylate iron salt is selected from a ferrous or a ferric salt or mixture thereof, such as, for example, ferric chloride, ferric sulphate, ferric nitrate, ferrous chloride, ferrous nitrate, ferrous sulphate, such as ferrous sulphate heptahydrate, and mixtures thereof. The salt may be anhydrous or a hydrate. For example, ferric chloride may be in the form of a hexahydrate and ferrous chloride in the form of a tetrahydrate.

The iron hydroxypyrone compounds formed by the method of the invention are preferably neutral complexes comprising iron cations and hydroxypyrone anions and without additional charge balancing anions, such as hydroxide or chloride. In one embodiment of the invention, the iron hydroxypyrone is an iron tri(hydroxypyrone) i.e., Fe(hydroxypyrone)$_3$, such as ferric tri(hydroxypyrone).

It has been found that ferrous salts can be oxidized in situ in the methods of the invention to provide ferric hydroxypyrone compounds.

In one embodiment of the invention, the iron hydroxypyrone compound provided by the method of the invention is a ferric trihydroxypyrone, where the hydroxypyrone is as defined herein, such as ferric trimaltol or ferric triethylmaltol.

By "neutral complex", it is intended to mean that the positive charge on the iron cation is balanced by the negative charge on the ligands in the complex. Therefore the total charge on the iron hydroxypyrone complex is zero. Because there is an internal balance of charges between the iron cation and the hydroxypyrone ligands, there is no need for any additional non-covalently bound anions, such as chloride, to balance any remaining charge on the iron cation.

The iron hydroxypyrone compound comprises iron in the ferric ($Fe^{3+}$) oxidation state.

In one embodiment of the invention, the iron hydroxypyrone, such as ferric trihydroxypyrone, produced by the method has a solubility in water or the aqueous solution at 25° C. of less than about 20 g/100 ml aqueous solution or water, such as less than about 10 g/100 ml aqueous solution or water, such as less than about 5 g/100 ml aqueous solution or water. For example, the solubility of the iron hydroxypyrone may be from about 1 g/100 ml aqueous solution or water to about 7 g/100 ml water, such as about 3 to 5 g/100 ml water or about 3.5 or 4 g/100 ml aqueous solution or water at 25° C. For example, the maximum solubility of ferric trimaltol in water is about 3.5 g/100 ml water at about 25° C.

When the iron is present in the ferric state, the neutral iron hydroxypyrone complex comprises hydroxypyrone and ferric iron in the stoichiometric ratio of 3:1 hydroxypyrone:ferric iron. The neutral complex of ferric iron and hydroxypyrone comprises three monobasic, bidentate hydroxypyrone ligands covalently bound to a ferric ion. The hydroxypyrone ligand is a bidentate ligand and is monobasic. The singly charged hydroxypyrone ligand contains an —O⁻ group in place of the —OH group present in the neutral hydroxypyrone ligand.

The hydroxypyrone ligands in the iron hydroxypyrone compounds may be the same or different. In a preferred embodiment, all of the hydroxypyrone ligands are the same.

Advantageously, the iron hydroxypyrone compound may be completely or substantially free of charged ferric hydroxypyrone complexes and neutral mixed ligand ferric complexes comprising covalently bound carboxylate ligands.

By "charged ferric hydroxypyrone complexes", it is intended to mean ferric hydroxypyrone complexes in which the stoichiometric ratio of hydroxypyrone to ferric iron is 2:1 or 1:1 so that the charge on the ferric cation is not internally balanced by the charge on the hydroxypyrone ligand. The total charge on the complex may be +1 or +2 and at least one counterion, such as, for example, chloride will be required in order to balance the charge.

By "substantially free", it is meant that the charged ferric complexes or neutral mixed ligand ferric complexes comprising carboxylate ligands comprise less than 10% by weight of the total weight of the iron species in the final composition, based on the composition, and preferably less than 5%, such as less than 2 wt. % or 1 wt. % or about 0 wt. %.

Where the iron hydroxypyrone compound has one or more chiral centres, the iron hydroxypyrone compound may be obtained as either pure enantiomer or diastereoisomer, a racemic mixture or a mixture enriched in either enantiomer or diastereoisomer. The mixture of enantiomers or diastereoisomers may be separated and purified using any of the known methods in the art. However, the mixture of optical isomers is typically not separated and purified.

Preferably, the hydroxypyrone used in the method of the present invention is a hydroxy-4-pyrone. It is particularly preferred if the hydroxy-4-pyrone is a 3-hydroxy-4-pyrone or a 3-hydroxy-4-pyrone in which one or more of the hydrogen atoms attached to the ring carbon atoms is replaced by an aliphatic hydrocarbon group having 1 to 6 carbon atoms.

The substituted 3-hydroxy-4-pyrones may comprise more than one type of aliphatic hydrocarbon group. However, it is generally preferred if there is substitution by one rather than two or three aliphatic hydrocarbon groups.

Alternatively, the hydroxypyrone ligand may be a 5-hydroxypyrone, such as Kojic acid (5-hydroxy-2-(hydroxymethyl)-4-pyrone). In a further embodiment, the hydroxypyrone used in the method of the present invention may comprise mixtures of the hydroxypyrone ligands mentioned above.

In one embodiment of the invention, the hydroxypyrone does not comprise a hydroxymethyl, hydroxyethyl or hydroxyalkyl substituent, where the alkyl is preferably $C_1$ to $C_{10}$, such as $C_1$ to $C_6$. In one embodiment of the invention, the hydroxypyrone does not comprise or consist of Kojic acid.

The term "aliphatic hydrocarbon group" is used herein to include both acyclic and cyclic groups that may be unsaturated or saturated, the acyclic groups having a branched chain or preferably a straight chain. Particularly preferred groups are those having from 1 to 4 carbon atoms, more preferably those having from 1 to 3 carbon atoms. Saturated aliphatic hydrocarbon groups are preferred, these being either cyclic groups such as the cycloalkyl groups cyclopropyl, and particularly cyclohexyl, or more preferably acyclic groups such as methyl, ethyl, n-propyl and isopropyl. Methyl and ethyl are particularly preferred.

Substitution at the 2- or 6-position is of particular interest, although, when the ring is substituted by the larger aliphatic hydrocarbon groups, there may be an advantage in avoiding substitution on a carbon atom alpha to the system. This system is involved in the formation of a complex with iron and the close proximity of one of the larger aliphatic hydrocarbons may lead to steric effects that inhibit complex formation.

Preferred hydroxypyrone ligands present in complexes according to the present invention have the formula (I), specific hydroxypyrones of particular interest have the formulae (II) and (III):

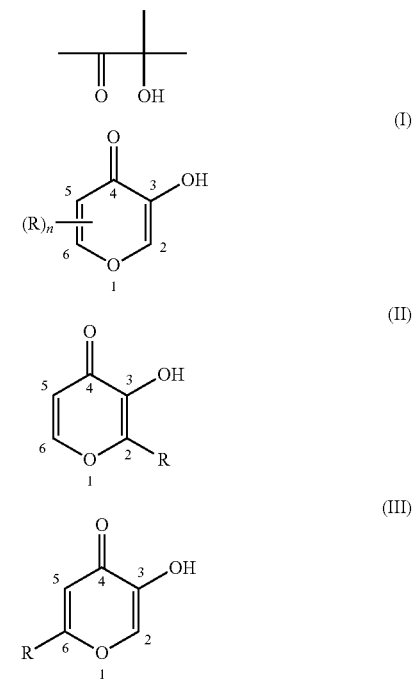

in which R is a cycloalkyl or alkyl group, for example, methyl, ethyl, n-propyl, isopropyl or butyl and n is 0, 1, 2 or 3 (the ring being unsubstituted by an alkyl group when n is 0).

Among these compounds, 3-hydroxy-2-methyl-4-pyrone (maltol; II, R=Me) is of most interest, whilst 3-hydroxy-4-pyrone (pyromeconic acid; I, n=0), 3-hydroxy-6-methyl-4-pyrone (isomaltol, III, R=Me) and particularly 2-ethyl-3-hydroxy-4-pyrone (ethylmaltol; II, R=Et) are also of especial interest. For convenience, the compound 3-hydroxy-2-methyl-4-pyrone is referred to herein as "maltol".

In one embodiment of the present invention the hydroxy-4-pyrone is selected from maltol, ethyl maltol and mixtures thereof. Maltol is most preferred and the iron hydroxypyrone compound of the invention is preferably ferric trimaltol.

Certain hydroxypyrones, such as maltol, are available commercially. With others, a convenient starting material in many instances consists of 3-hydroxy-4-pyrone, which is readily obtainable by the decarboxylation of 2,6-dicarboxy-3-hydroxy-4-pyrone (meconic acid). For example, 3-hydroxy-4-pyrone may be reacted with an aldehyde to insert a 1-hydroxyalkyl group at the 2-position, which group may then be reduced to produce a 2-allyl-3-hydroxy-4-pyrone. Other preparative methods are described by Spielman, Freifelder, J. Am. Chem. Soc. Vol. 69, Page 2908 (1947).

The skilled person will appreciate that these are not the only routes to these hydroxypyrone compounds and that various alternatives known in the art may equally be used.

In one embodiment of the invention, the precipitated iron hydroxypyrone obtainable by the method of the invention is pharmaceutically pure without the need for further purification. The precipitated iron hydroxypyrone may be separated and dried as described below but not further purified, such as by recrystallization. For example, the precipitated iron hydroxypyrone may have a purity of greater than or equal to about 95, 96, 97, 98, 99 or 99.5%.

In one embodiment, the isolated or separated precipitate comprising iron hydroxypyrone comprises iron hydroxide, such as $Fe(OH)_3$, in an amount of, for example, less than about 3, 2, 1 or 0.1 wt %. For example, the isolated or separated iron hydroxypyrone may comprise the iron hydroxide in an amount of from 0.01 to 3 wt. %, such as from 0.1 to 2.5 wt. %, preferably from 1 to 2 wt. %.

In one embodiment of the invention, the iron hydroxypyrone compound is an iron trihydroxypyrone, such ferric trihydroxypyrone, for example ferric trimaltol.

In one embodiment of the invention, the iron hydroxypyrone compound is precipitated from the aqueous solution to form a suspension comprising the precipitate and an aqueous solution, and the precipitate is separated and collected from the suspension and, optionally, dried. The drying conditions may be as described below.

The iron hydroxypyrone compound formed is generally isolated as a precipitate and optionally dried under ambient pressure, at for example 80° C. or greater, such as in an oven, or under a vacuum, where the temperature can be less than 80° C., for example 40° C. or less. The collected precipitate can, alternatively, be dried in an oven.

In one embodiment of the invention, the yield of the iron hydroxypyrone is greater than 50%, such as greater than 60%, 70%, 80%, 90% or 95% based on the starting materials.

The solubility of the iron hydroxypyrone compound, such as an iron trihydroxypyrone compound, in the aqueous solution, or aqueous alkaline solution, is generally such that it precipitates from solution at a pH of greater than 7. Not all of the formed iron hydroxypyrone may be precipitated although generally greater than 50% of the formed or available iron hydroxypyrone is precipitated. Typically, the iron hydroxypyrone species which is formed and precipitated is the iron trihydroxypyrone species which accounts for more than 50% of the iron hydroxypyrone compounds formed.

In one embodiment, from about 40% to 98%, such as from about 70% to 90%, by moles of the theoretical amount of the iron compound precipitates. The precipitate may be isolated or collected by separating the precipitated solid from the aqueous solution, or suspension comprising the aqueous solution, or liquid using techniques well known in the art, such as filtration, centrifugation and decantation, optionally under vacuum.

The precipitation of the iron hydroxypyrone compound may be enhanced by cooling the reaction mixture, using, for example, a cold water or ice and cold water bath, to cool the solution to a temperature of from 0° C. to 10° C.

In one embodiment of the invention, the precipitated and collected iron hydroxypyrone, such as ferric trihydroxypyrone, is optionally washed with a non-solvent, such as water, and dried, such as under vacuum. The drying can allow the iron hydroxypyrone to be isolated as a solid and this can be powdered. The water content of the dried iron hydroxypyrone powder is generally less than 10 wt. %, such as from 1 to 5 wt. %. No further purification may be carried out in general. Thus, the invention can provide a useful, pharmaceutically acceptable product without the need for further purification, such as evaporation and recrystallization or the use of organic solvents.

The supernatant liquid may include, for example, non-iron salts, such as sodium or potassium chloride salts, up to 100% by moles of the theoretical maximum, and iron hydroxypyrone compounds with differing molar ratios of iron:hydroxypyrone, such as 1:1 or 1:2. The supernatant liquid may optionally be separated from any solid by any suitable method, for example filtration, and dried at for example 80° C., preferably to a constant weight.

The iron hydroxypyrone compounds are optionally dried, as described herein, and may be purified further and isolated as substantially pure products according to the methods known in the art such as, for example, recrystallisation. Recrystallisation may be carried out using solvents such as, for example, water, an alcohol such as ethanol, aqueous alcoholic mixtures, or mixtures of aqueous solvent mixtures comprising an ether such as, for example, diethyl ether or tetrahydrofuran. Typically, however, the iron hydroxypyrone compound is not purified after being isolated as a precipitate and, optionally, dried.

In one aspect, the invention provides a pharmaceutical composition comprising an iron hydroxypyrone compound and an iron hydroxide, such as ferric hydroxide or $Fe(OH)_3$.

In one embodiment of the invention, the iron hydroxide is non-therapeutic or pharmaceutically inactive, for example the iron hydroxide may be inert. In a preferred embodiment of the invention, the iron hydroxide is in the form of a solid in the composition (i.e., not a liquid or colloid). Preferably, the iron hydroxide is non-therapeutic or pharmaceutically inactive and in the form of a solid.

The iron hydroxide is preferably present as a pharmaceutical excipient. For example, the iron hydroxide, such as ferric hydroxide, may provide the composition with a stable colour, such as red, pink or brown or shades thereof in the same region of the spectrum. By "stable colour" it is intended to mean that the composition does not substantially change colour when exposed to ambient conditions of temperature and humidity over a period of, for example, 1 day, 1 week or 1 month.

In one embodiment of the invention, the composition comprises a taste additive, such as unreacted hydroxypyrone, for example maltol, which is uncomplexed. The unreacted hydroxypyrone may be a taste additive. The use of the unreacted hydroxypyrone can provide a beneficial taste enhancement (such as a caramel flavour) to the iron hydroxypyrone compound. For example, ferric trimaltol is mildly metallic in flavour but also caramelic. Iron salts such as ferric chloride have an astringent taste and can be unacceptable for oral administration for this reason alone.

In one embodiment of the invention, the iron hydroxide does not comprise a colloidal iron, such as colloidal iron hydroxide, and/or a sugar protected form of an iron hydroxide, such as ferric hydroxide saccharate.

By the term "pharmaceutical composition", it is intended to mean a composition which is suitable for administration to a subject. By the term "subject" we include an animal, such as a mammal, for example a human.

The iron hydroxypyrone compound may be as defined in any of the above embodiments. In one embodiment, the iron hydroxypyrone compound is a ferric trihydroxypyrone, such as, for example, ferric trimaltol or ferric triethylmaltol.

The iron hydroxypyrone, such as ferric trihydroxypyrone, may be present in the composition in an amount of at least about 40 wt. % based on the weight of the composition, such as at least about 50, 60, 70, 80, 90 or 95 wt. %, and may be pharmaceutically pure as defined herein. For example, the iron hydroxypyrone, as defined herein, may be present in an amount of from about 40 to about 99 wt. %, such as from about 60 to about 98 wt. % or from about 70 to about 95 wt. %.

The composition optionally further comprises a hydroxypyrone compound, such as maltol, ethyl maltol and mixtures thereof, and/or a carboxylic acid, such as, for example, citric acid. In addition, the composition may comprise a non-iron salt of an inorganic anion, such as sodium or potassium chloride. These optional components may be independently present in an amount of less than 10 wt. %, such as less than or equal to about 5 wt. % or about 2 wt. %. For example, the hydroxypyrone and/or non-iron salt may be present in the composition in an amount of from 0.01 to 2 wt. %, such as from 0.1 to 1 wt. %.

In one embodiment, the composition is in the form of a solid, such as, for example, a powder, capsule or tablet. In one embodiment, the composition is not in the form of a gum.

Typically, the iron hydroxide, such as ferric hydroxide, is present in the composition in an amount of less than or equal to about 10 wt. % based on the weight of the composition, such as less than or equal to about 5 wt. % or about 2 wt. %. For example, the iron hydroxide may be present in the composition in an amount of from 0.01 to 2 wt. %, such as from 0.1 to 1 wt. %.

The composition may be obtained according to the methods of the invention or, for example, by mixing the iron hydroxypyrone compound and iron hydroxide.

In a further aspect, the present invention relates to a pharmaceutical composition according to the invention together with a pharmaceutically acceptable diluent or carrier.

The compositions of the present invention may further comprise one or more carboxylic acids. The acid may be selected from any of the carboxylic acids described in WO 03/097627 and is preferably pharmaceutically acceptable and suitable for use in medicine.

The acid may be added in order to optimise the buffering efficiency of the iron compositions of the present invention in aqueous solution and/or in vivo.

Preferably, the molar ratio of carboxylic acid to iron hydroxypyrone in the composition of the invention is in the range of from 30:1 to 1:30, more preferably from 10:1 to 1:10.

By "pharmaceutically acceptable" we include the normal meaning that the carriers must be "acceptable" in the sense of being compatible with the active ingredient (the iron hydroxypyrone compound) and not deleterious to the recipients thereof.

The composition may be in the form of a solid, such as a powder, capsule or tablet, or liquid. Suitable solid diluents and carriers include starch, dextrin and magnesium stearate. Stabilising and suspending agents such as methylcellulose and povidone and other tableting agents such as lactose and flow aids such as Aerosil 2000™ may also be used.

Particularly useful diluents and carriers are wetting agents or surfactants, preferably non-ionic or ionic surfactants. Examples of suitable non-ionic surfactants include polyoxyl-10-oleyl ether and polysorbates. An example of a suitable ionic surfactant is sodium lauryl sulfate.

Liquid carriers may be sterile and pyrogen free: examples are saline and water.

The iron hydroxypyrone compounds and compositions of the present invention provide particular advantages in relation to the formulation of iron complexes. Liquid formulations of the iron compounds are particularly suitable for oral and parenteral administration. In such applications, the solubility of some known iron complexes is unsatisfactory.

The iron hydroxypyrone compounds and compositions may be formulated with a physiologically acceptable diluent or carrier for use as pharmaceuticals for veterinary or human use in a variety of ways. However, compositions in which the diluent or carrier is other than a non-sterile solution in water and/or an organic solvent are generally preferred. Thus, the iron complexes may be applied as an aqueous, oily or emulsified composition incorporating a liquid diluent, which will, however, most usually be employed for parenteral administration and therefore may conveniently be sterile and pyrogen free. One form of composition of particular interest thus has the form of a sterile, injectable solution. Oral administration is, however, more generally to be preferred for the treatment of iron deficiency anaemia in humans, and the compositions of the present invention may be given by that route.

For oral administration in humans it is more usual to use compositions incorporating a solid carrier, for example, starch, lactose, dextrin or magnesium stearate. Such solid compositions may conveniently be shaped, for example in the form of tablets, capsules (including spansules), etc. However, liquid preparations are especially useful for oral administration to patients who have difficulty in swallowing solid forms. Such difficulties are common in patients suffering from anaemias associated with arthritis.

Other forms of administration than by injection or through the oral route may also be considered, for example the use of suppositories.

More than one iron hydroxypyrone compound obtained by the method of the present invention may be contained in a pharmaceutical composition and other active compounds may also be included. Typical additives include compounds having the ability to facilitate the treatment of anaemia, such as folic acid. A zinc source may also be included.

Preferably the above compositions are suitable for use in medicine.

The compositions of the present invention are particularly useful for serious anaemias arising from bleeding disorders, particularly of the gastrointestinal tract. Many of the patients with such disorders are intolerant of standard ferrous anti-anaemia compounds. Ferrous preparations are contra-indicated or the subject of warnings in such conditions. Furthermore, patients who may need blood transfusions or in-patient treatment with intravenous injections can be treated on an outpatient basis saving substantial costs of treatment.

The pharmaceutical compositions of the invention may be used in a method for the treatment of a subject to effect an increase in the levels of iron in the subject's bloodstream and/or the prevention and/or treatment of anaemia, such as iron-deficiency anaemia, which comprises administering to said subject an effective amount of composition as defined previously.

The iron hydroxypyrone compounds and compositions obtainable by the method of the present invention may also be used in the treatments described in WO 2009/138761.

The listing or discussion of an apparently prior-published document in this specification should not necessarily be taken as an acknowledgement that the document is part of the state of the art or is common general knowledge.

The following non-limiting examples illustrate the invention and do not limit its scope in any way. In the examples and throughout this specification, all percentages, parts and ratios are by weight unless indicated otherwise. Average molecular weights are based on weight unless otherwise specified. It will be appreciated that the various percentage amounts of the different components that are present in the products of the invention, including any optional components, will add up to 100%.

EXAMPLES

In the examples ferric chloride was either used as a freshly prepared solution or as a solid form.

Comparative Example 1

Preparation of Iron Trimaltol from Pure Maltol

Maltol was dissolved in an aqueous solution of ferric chloride and ferric trimaltol was precipitated upon the addition of sodium hydroxide.

An accurate mass of ferric chloride hexahydrate granules (330 g) was dissolved in distilled water to yield a pH of 0.6. To this solution, an equimolar amount of maltol was added (490 g in total, initially 250 g) and allowed to dissolve with continuous stirring. The pH of this solution was found to be zero and the colour of this solution was deep-purple. Spectroscopy showed that the initial solution was mainly a 1:1 Fe/maltol mixture with some 1:2 component. The remaining maltol was added. After an hour of stirring, sodium hydroxide (147 g NaOH in 750 ml water) was added dropwise to the solution until a pH of 8.3 was achieved. The solution and precipitate were red. The precipitate was collected using a Buchner funnel under vacuum. The precipitate was dried at 40° C. under vacuum.

Maltol is only slightly soluble in an aqueous acidic reaction medium. After an hour of stirring, traces of undissolved maltol were visible on the surface of the ferric chloride/maltol solution, on the walls of the reaction vessel and on the stirrer. Upon addition of sodium hydroxide, there appeared to be lumps of a brownish-black substance on the walls of the reaction vessel and on the stirrer which seemed to add to the impurities in the desired product.

An attempt to heat the ferric chloride/maltol solution so as to assist the maltol to dissolve in the ferric chloride solution resulted in a burnt, off spec, colour iron maltol sample. This method also produces two by-products which consume expensive maltol namely $Fe(OH)_2(Maltol)$ and $Fe(OH)(Maltol)_2$.

The sodium hydroxide solution has to be added extremely slowly to prevent "gumming up" and formation of undesirable lumps at the bottom of the reaction vessel.

A yield of about 78% ferric trimaltol was obtained using this method of preparation.

When maltol is added to a ferric chloride solution at a low pH, no ferric trimaltol is formed and ferric hydroxide is generated with ferric monomaltol and a small percentage of ferric dimaltol species. The charge neutralisation of these complexes is either the hydroxyl functional group or the chloride anion. This addition also results in the formation of black deposits and gums consisting of ferric chloride/ferric hydroxide polymers. These black deposits are also produced if the solutions are heated. Therefore it is not possible to obtain the correct stoichiometry for the formation of ferric trimaltol and manufacture a pharmaceutically acceptable product using this method.

The addition of maltol to an aqueous solution of ferric or ferrous chloride was deemed impractical for scale up and manufacturing purposes and Examples 2 to 4 investigate the addition of the iron chlorides to maltol in solution.

The Problem of Working in an Aqueous Environment

Ferric chloride as a hydrated ion in aqueous solution is a strong Lewis acid with a Ka of $7 \times 10^{-3}$ and ferrous chloride as a hydrated ion in aqueous solution is also a strong Lewis acid with a Ka of $5 \times 10^{-9}$. Over the desired range for using iron chlorides as starting materials for the synthesis of ferric trimaltol, ferric chloride in aqueous solution has a pH value in the range of 1-3 and ferrous chloride has a pH in the range of 3-5. Furthermore, commercial solutions of iron chlorides have a pH circa 1 because they are stabilised by the addition of hydrochloric acid to prevent the precipitation of ferric hydroxide species.

The present invention recognises that maltol is virtually insoluble at these low pH values and has limited solubility when dissolved in water in the pH range 6-8. The maximum aqueous solubility is 1 g/100 ml at 20° C. However, the solubility of maltol can be increased to 10 g/100 ml by heating to near boiling temperatures. Maltol is stable in aqueous solution at these temperatures and this property has been employed in Example 4 to synthesise ferric trimaltol. At low pH values ferric trimaltol is not the preferred species due to disproportionation.

In order to obtain significant amounts of ferric trimaltol using a stoichiometric ratio of iron salt to hydroxypyrone of 1:3, the eventual pH of the solution must exceed 7 since below that pH ferric dimaltol and monomaltol species will exist. Therefore two methods of increasing the pH were researched 1) using sodium carbonate and 2) using sodium hydroxide. Other alkali hydroxides could be used such as potassium hydroxide. The sodium carbonate neutralisation was found to be less preferable due to $CO_2$ generation.

This research lead to an improved synthesis of ferric trimaltol.

Example 2

Maltol was dissolved in an aqueous solution of sodium hydroxide and iron maltol was precipitated upon the addition of ferric chloride.

In view of some of the difficulties experienced in Example 1, and the fact that maltol is very soluble in aqueous alkali hydroxide solutions, it was decided to change the manufacturing procedure.

The initial work using this method of preparation showed that a 90% yield was achieved. Various operating parameters were then optimised and the following procedure outlines the final method chosen. A yield of 95% was then achieved.

An accurate mass of sodium hydroxide pellets (20 g) was dissolved in distilled water to yield a pH of 13.50. An equimolar amount of maltol (63 g) was added to this aqueous solution of NaOH to give a clear yellow coloured solution with a pH of 11.6. Almost immediately a stoichiometric amount of ferric chloride (45 g) was added slowly to this solution to give a pH of 7.1 and a red precipitate formed, which was then collected using a Buchner funnel under vacuum. The precipitate was then dried at 40° C. under vacuum.

Adding the maltol solution in sodium hydroxide to ferric chloride as in method 1 is not preferred since it gives an off spec product and gums and a black precipitate.

Maltol is very soluble in aqueous alkali hydroxide solutions giving a yellow solution. The concentration of the hydroxide solution preferably does not exceed 20%.

This method is advantageous since it has the potential to produce only one by-product viz, ferric hydroxide $Fe(OH)_3$ which consumes some of the iron intended to complex with the maltol. This is not easily measurable in the presence of iron maltol and so the following method was used to measure the ferric hydroxide.

$Fe(OH)_3$ is insoluble in ethanol and so the iron maltol product was dissolved in ethanol. It was found that small amounts of $Fe(OH)_3$ may be present in the batches of iron maltol synthesized according to Example 2.

Taking the extremes of the specification, in one embodiment, the amount of $Fe(OH)_3$ present in the active material may not exceed 2 wt. % $Fe(OH)_3$ based on the total weight of the composition. In view of its well known inert characteristics the level of this compound is adequately controlled and a final specification including controlled ferric hydroxide should be acceptable.

The mass balance for maltol and iron was closed at 99%.

A yield of 95% iron maltol was obtained using this method of preparation.

Example 3

Maltol was dissolved in an aqueous solution of Sodium Carbonate and Iron Maltol was precipitated upon the addition of Ferric Chloride.

An accurate mass of sodium carbonate ($Na_2CO_3$) (53 g) was dissolved in distilled water to give a solution having pH=11.5. An equimolar amount of maltol (65 g) was added to this aqueous alkali solution to give a murky creme coloured solution of pH=9.9. A stoichiometric amount of a ferric chloride solution was added drop wise to this solution to a pH of 8.00. A further 15 grams of $Na_2CO_3$ was added to this solution to increase the pH to 9.00. The remainder of the ferric chloride solution was then added to give a solution pH=8.77 and a red coloured precipitate appeared.

The precipitate was collected using a Buchner funnel under vacuum. The precipitate was then dried at 40° C. under vacuum. The release of $CO_2$ during the reaction tends to make this process less desirable due to foaming on the surface. The final product is a gel-like solid when wet and the removal of moisture during drying can therefore be time consuming. The process may not be preferred but the ferric trimaltol produced could be acceptable.

Example 4

Maltol was dissolved in water and heated to a near boiling temperature and ferric or ferrous chloride was added to form a 1:1/1:2 mixture of ferric maltol. The solution was allowed to cool and was added to maltol dissolved in sodium hydroxide.

Stage 1

Depending on the batch size required, the ferric chloride was added slowly to a maltol solution in water at a pH of 6-7. The solubility of maltol is greatly enhanced up to 10 g/100 ml by heating to temperatures above 60° C. Addition of ferric chloride or ferrous chloride and monitoring the pH of the solution and maintaining the pH>3 mainly produces ferric dimaltol species but very little ferric trimaltol. Above pH 3, no ferric hydroxide appeared to be generated. Ferric monomaltol and dimaltol species either with hydroxy or chloride giving the charge neutralisation are very soluble and a concentrated solution in excess of 30 g/100 ml can be generated. In order to obtain the correct stoichiometry for the formation of ferric trimaltol, further maltol is required and the pH needs to be corrected to values higher than 7.

As anhydrous ferrous or ferric chloride either 126 g or 162 g in 200 ml of water can be added to a liter of water containing 120 g of maltol. This ratio of iron to maltol does not provide sufficient maltol to produce any significant amounts of ferric trimaltol which does not precipitate at this stage.

Stage 2

Maltol in alkaline solution has been described as set out above. Conveniently, because maltol solutions up to 20% in sodium hydroxide have a pH circa 11.6, mixing of this solution with the ferric mono/dimaltol solutions from stage 1 yields a precipitate of ferric trimaltol with a deep characteristic burgundy red colour of high purity as determined by UV-vis spectroscopy. The filtrate yields product which is suitable for a GMP (good manufacturing process). The sodium chloride which is generated by this process is found in the supernatant since it has a much higher solubility at 35 g/100 ml than ferric trimaltol. The small amounts of sodium chloride in the ferric trimaltol can be reduced, if required, by washing in water.

A further, surprising feature of the research resulted from work on ferrous chloride. Ferrous chloride may be substituted in stage 1 to form ferric dimaltol since the maltol was found to auto-oxidise the ferrous to ferric during the process of chelation. One aspect of this work which was considered to be potentially very useful if larger batch sizes were required arose from the finding that being a weaker Lewis acid than ferric chloride the pH of the starting solution was in excess of 3. Therefore the risk of generating ferric hydroxide was lower than with the use of ferric chloride at higher concentrations.

Ferrous and ferric chloride in solution or as a solid may be added to an alkaline solution of maltol in sodium hydroxide, combining stages 1 & 2. Providing a small excess of maltol up to about 10% is added then a precipitate of ferric trimaltol with a small amount of maltol is obtained. Such a preparation would be satisfactory as a GMP ferric trimaltol product.

The invention claimed is:

1. A method of forming iron tri(maltol) comprising:
   combining maltol with an aqueous solution having a pH of 3 to about 7;
   heating the combined maltol and aqueous solution to form a heated maltol solution having a pH of 3 to 7;
   combining the heated maltol solution with a non-carboxylate iron salt to form a solution having a pH of 3 to 7;
   combining the solution having a pH of 3 to 7 with an aqueous alkaline solution comprising maltol, wherein the aqueous alkaline solution has a pH of greater than 7; and
   precipitating iron tri(maltol) from the combined solutions having a pH of greater than 7.

2. The method of claim 1, wherein the non-carboxylate iron salt is selected from a ferrous or a ferric salt and mixtures thereof.

3. The method according to claim 1, wherein the aqueous solution comprises water in an amount of greater than 30% v/v of the total solution.

4. The method according to claim 1, wherein the precipitate is separated and collected and, optionally, dried.

5. A method of forming iron tri(maltol) comprising:
   forming an aqueous solution having a pH of less than 7 comprising iron monomaltol, iron di(maltol), or a mixture thereof by combining a non-carboxylate iron salt with a maltol solution having a pH of less than 7;
   adding further maltol to the aqueous solution having a pH of less than 7;
   increasing the pH of the aqueous solution to greater than 7; and
   precipitating the iron tri(maltol) from the aqueous solution having a pH of greater than 7.

6. The method according to claim 5 wherein the further maltol is in an aqueous alkaline solution.

7. The method of claim 5, wherein the non-carboxylate iron salt is selected from a ferrous or a ferric salt and mixtures thereof.

8. The method according to claim 5, wherein the aqueous solution comprises water in an amount of greater than 30% v/v of the total solution.

9. The method according to claim 5, wherein the precipitate is separated and collected and, optionally, dried.

* * * * *